(12) United States Patent
Hirota et al.

(10) Patent No.: US 7,894,654 B2
(45) Date of Patent: Feb. 22, 2011

(54) VOICE DATA PROCESSING FOR CONVERTING VOICE DATA INTO VOICE PLAYBACK DATA

(75) Inventors: Shin Hirota, Tokyo (JP); Yoshihiro Oda, Tokyo (JP); Tetsu Miyagawa, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/498,648

(22) Filed: Jul. 7, 2009

(65) Prior Publication Data

US 2010/0008556 A1     Jan. 14, 2010

(30) Foreign Application Priority Data

Jul. 8, 2008    (JP)    ............................. 2008-177727

(51) Int. Cl.
*G06K 9/00*     (2006.01)
*G10L 21/00*    (2006.01)

(52) U.S. Cl. .................. 382/131; 382/100; 382/190; 704/216

(58) Field of Classification Search ................ 382/100, 382/131, 181, 190; 704/216
See application file for complete search history.

(56) References Cited

U.S. PATENT DOCUMENTS

| | | | |
|---|---|---|---|
| 6,944,510 B1 | 9/2005 | Ballesty et al. | |
| 7,006,970 B2 * | 2/2006 | Jinnai et al. | 704/239 |
| 7,283,954 B2 | 10/2007 | Crockett et al. | |
| 7,313,519 B2 | 12/2007 | Crockett | |
| 7,337,109 B2 * | 2/2008 | Wu | 704/218 |
| 7,461,002 B2 * | 12/2008 | Crockett et al. | 704/278 |
| 7,479,594 B2 | 1/2009 | Matsuura et al. | |
| 7,507,894 B2 | 3/2009 | Matsuura et al. | |
| 2005/0234712 A1 * | 10/2005 | Dong et al. | 704/207 |
| 2006/0107821 A1 * | 5/2006 | Matsuura et al. | 84/603 |

FOREIGN PATENT DOCUMENTS

| | | |
|---|---|---|
| EP | 0865026 A2 | 9/1998 |
| JP | 08-287612 | 11/1996 |
| JP | 2005-266571 | 9/2005 |

* cited by examiner

*Primary Examiner*—Bhavesh M Mehta
*Assistant Examiner*—Stephen R Koziol
(74) *Attorney, Agent, or Firm*—Armstrong Teasdale LLP

(57) ABSTRACT

A voice data processing apparatus which converts voice data to voice playback data by an OLA method to correspond to a set magnification of playback velocity, including a voice data block setting device which partitions the voice data to set a plurality of voice data blocks, a segment setting device which sets voice data segments to the voice data to correspond to respective voice data blocks, a segment adjuster which adjusts positions and lengths on a time base, of the voice data segments set by the segment setting device, and a voice playback data generator which combines the respective voice data segments adjusted by the segment adjuster so as to overlap each other along the time base thereby generating the voice playback data.

20 Claims, 13 Drawing Sheets

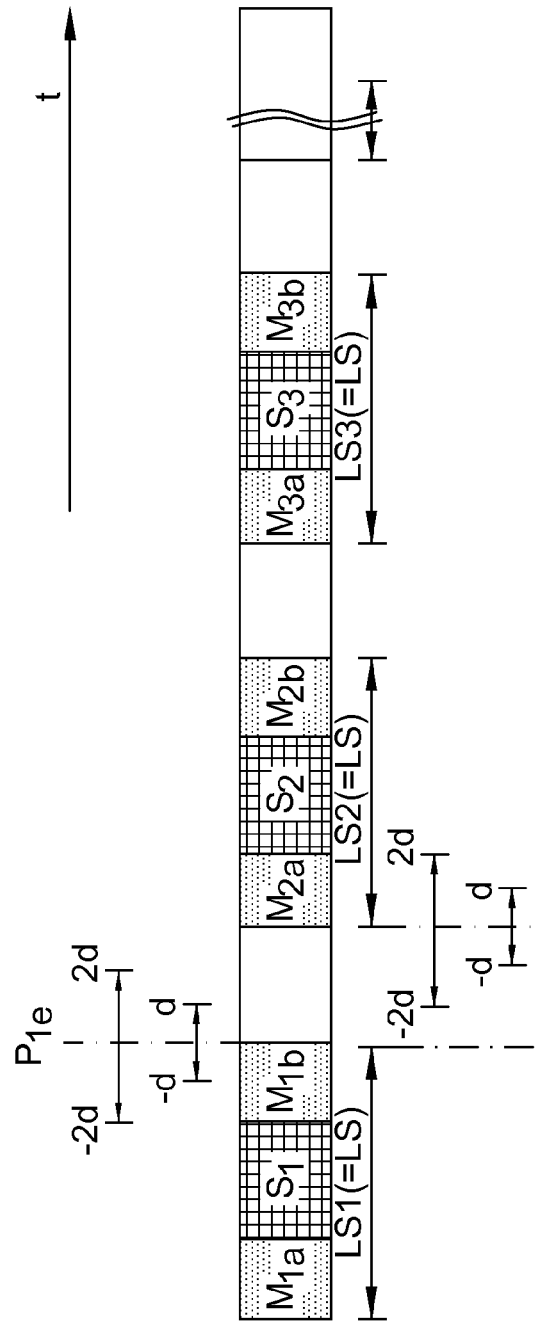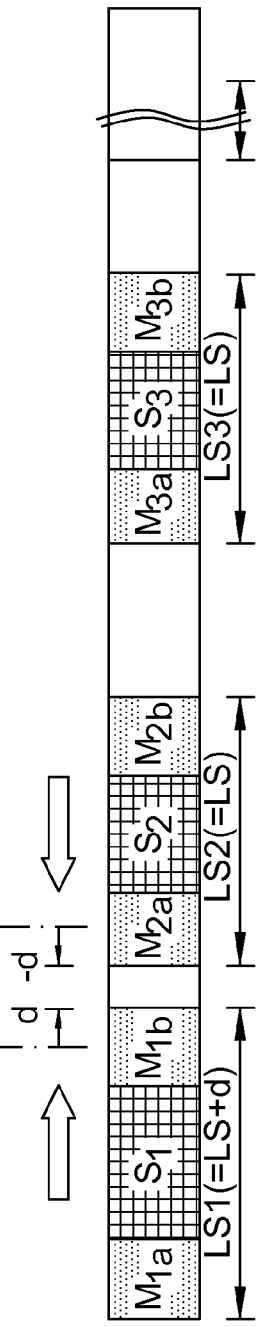
FIG. 4D
FIG. 4E

FIG. 5

| | | POSITION Pne OF END POINT Sn OF VOICE DATA SEGMENT | | | | |
|---|---|---|---|---|---|---|
| | | -2d | -d | 0 | +d | +2d |
| POSITION P(n+1)s OF START POINT OF VOICE DATA SEGMENT Sn+1 | -2d | Sm(-2d,-2d) | Sm(-d,-2d) | Sm(0,-2d) | Sm(+d,-2d) | Sm(+2d,-2d) |
| | -d | Sm(-2d,-d) | Sm(-d,-d) | Sm(0,-d) | Sm(+d,-d) | Sm(+2d,-d) |
| | 0 | Sm(-2d,0) | Sm(-d,0) | Sm(0,0) | Sm(+d,0) | Sm(+2d,0) |
| | +d | Sm(-2d,+d) | Sm(-d,+d) | Sm(0,+d) | Sm(+d,+d) | Sm(+2d,+d) |
| | +2d | Sm(-2d,+2d) | Sm(-d,+2d) | Sm(0,+2d) | Sm(+d,+2d) | Sm(+2d,+2d) |

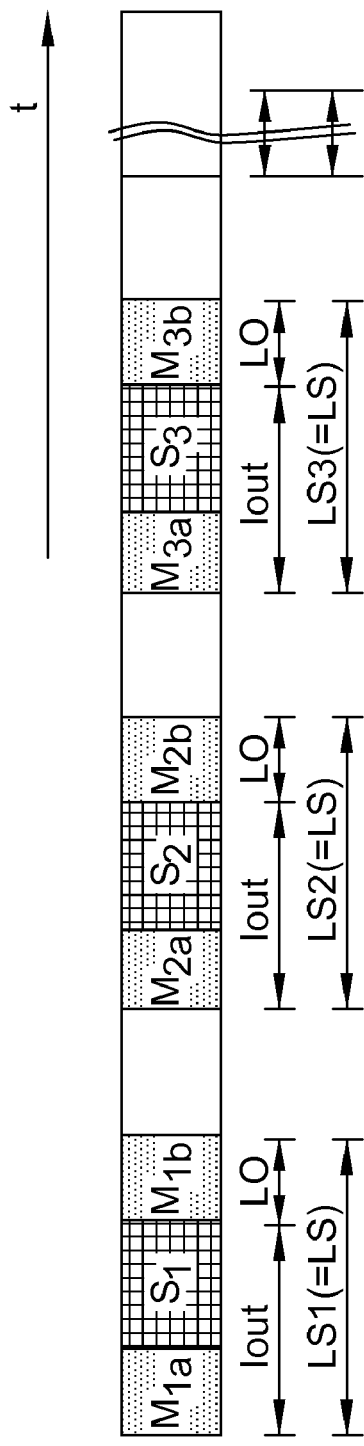
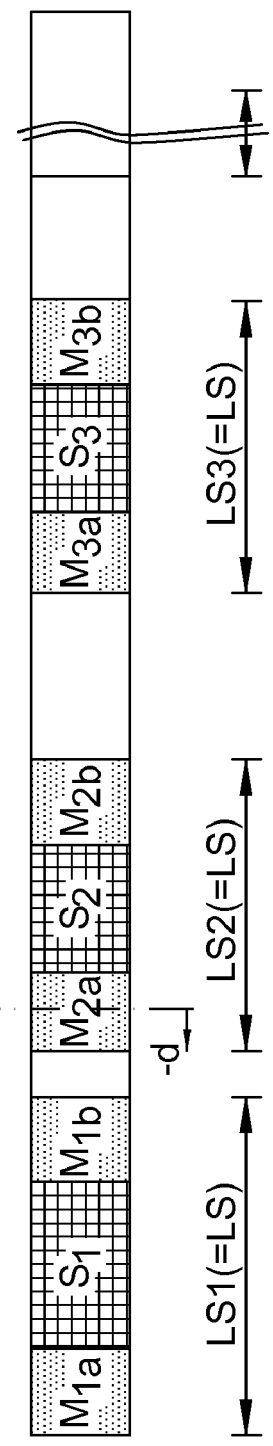
FIG. 7A
FIG. 7B

VOICE DATA PROCESSING FOR CONVERTING VOICE DATA INTO VOICE PLAYBACK DATA

CROSS REFERENCE TO RELATED APPLICATIONS

This application claims the benefit of Japanese Patent Application No. 2008-177727 filed Jul. 8, 2008, which is hereby incorporated by reference in its entirety.

BACKGROUND OF THE INVENTION

The embodiments described herein relate to a voice data processing apparatus, a voice data processing method and an imaging apparatus. More particularly, the embodiments described herein relate to a voice data processing apparatus and a voice data processing method both of which convert voice data to voice playback data so as to correspond to a magnification of a playback speed or velocity at the reproduction of the voice data by an OLA (Overlap-Add) method. The embodiments described herein also relate to an imaging apparatus including the voice data processing apparatus.

An imaging apparatus such as a magnetic resonance imaging (MRI) apparatus executes scans on a photographing or imaging area of a subject thereby to execute imaging on the photographing area.

For example, the magnetic resonance imaging apparatus transmits each RF pulse to the imaging area of the subject in an imaging space formed with a static magnetic field thereby to excite spins of proton in the imaging area by a nuclear magnetic resonance (NMR) phenomenon and receives magnetic resonance (MR) signals generated by the excited spins. Thereafter, the magnetic resonance signals obtained by the scan's execution are used as raw data to generate a magnetic resonance image about the imaging area of the subject.

There is a case in which in such an imaging apparatus, body-motion artifacts occur in an image generated about a subject corresponding to a living body such as a human body due to the fact that body motion such as breathing exercises occur in the subject upon execution of each scan.

Therefore, when imaging is carried out, respiration guide information for guiding the breathing exercises is transmitted to the subject held in the imaging space by voice to prevent the occurrence of body motion due to the breathing, for example.

For example, voice data indicating that the subject is caused to stop breathing is automatically reproduced/outputted and instructed prior to the start of each scan so as to match with the timing provided to execute the scan. Namely, the respiration guide information is transmitted to the subject by voice using a so-called Auto Voice function.

There is a case in which upon the reproduction/output of the voice data as described above, the magnification of a playback velocity for the voice data is changed.

There is a case in which in the imaging apparatus, for example, the magnification of the playback velocity for the voice data is changed to complete the playback of voice indicative of the respiration guide information during a period in which a contrast agent is injected into the blood flowing in the subject and the injected contrast agent reaches the imaging area in which the imaging is executed on the subject.

Here, data processing for converting the voice data to voice playback data so as to correspond to the set magnification of playback velocity is executed and the converted voice playback data is reproduced and outputted.

When the playback speed is changed, the musical pitch of the voice generally changes. Described concretely, when the magnification of the playback velocity is raised (the playback velocity is accelerated), the voice is high pitched, whereas when the magnification of the playback velocity is reduced (the playback velocity is made slow), the voice is low pitched. There is a case in which it is not easy for the subject to hear the reproduced voice accurately because the musical pitch of the voice reproduced in this way changes, thus encountering difficulties in executing imaging efficiently.

In order to improve such an imperfection or problem, an OLA method has been known as a method for suppressing a change in musical pitch (refer to, for example, Japanese Unexamined Patent Publication No. Hei 08(1996)-287612, Japanese Unexamined Patent Publication No. 2005-266571, and European Patent EP 0865026).

A WSOLA (Waveform Similarity Overlap-Add) method has been known as a method for further improving the OLA method (refer to, for example, W. Verhelst, M. Roelands, "An Overlap-Add Technique Based on Waveform Similarity (WSOLA) for High Quality Time-Scale Modification of Speech", Acoustics, Speech, and Signal Processing, 1993. ICASSP-93.).

FIGS. 6A through 6E are respectively diagrams showing data processing for converting voice data to voice playback data so as to correspond to a magnification of a playback velocity at the reproduction of the voice data by an OLA method.

In the OLA method, voice data D is inputted as shown in FIG. 6A. Thereafter, a plurality of voice data blocks $B_n$ (where n=1, 2, ..., i)(where i: integer) are set to the voice data D as shown in FIG. 6B.

Here, the voice data D is set in such a manner that lengths (time intervals) Iin on a time base, of the respective voice data blocks $B_n$ become identical to one another.

Described concretely, each of the lengths Iin of the voice data blocks $B_n$ is defined to be a value obtained by multiplying a predetermined value Iout by a playback-velocity magnification V. For example, the predetermined value Iout is assumed to be 90 ms and the length Iin of each voice data block $B_n$ is assumed to be 180 ms when the playback velocity is set to a playback velocity equal to twice a reference velocity.

Next, as shown in FIG. 9(c), a plurality of voice data segments $S_n$ (where n=1, 2, ..., i)(where i: integer) are set to the voice data D so as to correspond to the set voice data blocks $B_n$.

Here, the start point of the time base for each voice data segment $S_n$ corresponds to the start point of the time base for each voice data block $B_n$. Further, the respective voice data segments $S_n$ are defined such that the lengths $LS_n$ thereof on the time base become identical.

Here, as shown in FIG. 6D, an area or region between the start point of the time base and the point of time at which a predetermined time has elapsed therefrom is set as a first overlap area $S_{na}$ (where n=1, 2, ..., i)(where i: integer) at each of the voice data segments $S_n$ set as described above. At each of the voice data segments $S_n$, an area or region from the end point of the time base to the point of time at which a predetermined time is retraced therefrom is set as a second overlap area $S_{nb}$ (where n=1, 2, ..., i)(where i: integer).

Described concretely, the value obtained by adding the length LO of each of the overlap areas $S_{na}$ and $S_{nb}$ to a predetermined value Iout is set as the length LS of each voice data segment $S_n$. Assuming that for example, the predetermined value Iout is 90 ms and the length LO of each of the overlap areas $S_{na}$ and $S_{nb}$ is 10 ms, the length LS of each voice data segment $S_n$ is set as 100 ms.

Next, as shown in FIG. 6E, the first and second overlap areas $S_{(n-1)a}$ and $S_{nb}$ set to the voice data segments $S_n$ are combined so as to overlap each other thereby to generate voice playback data DS.

Described concretely, the second overlap area $S_{1b}$ set to the first voice data segment $S_1$, and the first overlap area $S_{2a}$ set to the second voice data segment $S_2$ sided with the first voice data segment $S_1$ along the time base are combined so as to overlap each other. The respective voice data segments $S_n$ are processed sequentially in like manner. Namely, data processing is repeated in such a manner that after similar processing has been executed on the second voice data segment $S_2$ and the third voice data segment $S_3$, the third voice data segment $S_3$ and the fourth voice data segment $S_4$ are subjected to the similar processing, whereby voice playback data DS is generated.

Here, voice data in the second overlap area $S_{nb}$ provided in a stage subsequent to each of the respective voice data segments $S_n$, and voice data in the first overlap area $S_{(n+1)a}$ provided in a stage prior to its subsequent voice data segment $S_{n+1}$ are combined, to normalize power of voice data in the mutual overlap areas $S_{na}$ and $S_{(n+1)b}$. For example, a trapezoidal window function is added up to the respective voice data segments $S_n$, followed by execution of their combination.

Therefore, according to the OLA method, a change in the musical pitch at the time that the playback velocity is changed can be suppressed.

In the OLA method, however, there is a case in which the waveform of the voice data in the second overlap area $S_{nb}$ of each voice data segment $S_n$ is different markedly from the voice data in the first overlap area $S_{(n+1)a}$ caused to overlap with its subsequent voice data segment $S_{n+1}$. Therefore, there is a case in which the voice combined in the mutually-related overlap areas $S_{nb}$ and $S_{(n+1)a}$ becomes unnatural.

In order to improve such an imperfection or problem, there has been proposed a WSOLA method in which the OLA method has been improved.

FIGS. 11 and 12 are respectively diagrams showing data processing for converting voice data to voice playback data so as to correspond to a magnification of a playback velocity taken upon reproduction of voice data by the WSOLA method.

In the WSOLA method in a manner similar to the OLA method, the voice data blocks $B_n$ have been set to the voice data D as shown in FIGS. 6A through 6C. Thereafter, voice data segments $S_n$ are set so as to correspond to the respective set voice data segments $B_n$.

However, in the WSOLA method unlike the OLA method, the position on the time base, of the voice data segment $S_{n+1}$ following each voice data segment $S_n$ is adjusted after the execution of Steps shown in FIGS. 6A through 6C in such a manner that the waveform of voice data in an area including the second overlap area $S_{nb}$ at each voice data segment $S_n$ and the waveform of voice data in an area including the first overlap area $S_{(n+1)a}$ at the voice data segment $S_{n+1}$ approximate each other. Namely, the voice data segment $S_{(n+1)}$ is moved in such a manner that similarity indicative of a resemblance between the waveform of the voice data in the area including the second overlap area $S_{nb}$ at the voice data segment $S_n$, and the waveform of the voice data in the area including the first overlap area $S_{(n+1)a}$ at its subsequent voice data segment $S_{n+1}$ becomes large.

Described concretely, as shown in FIG. 7A, an area in which a predetermined time has elapsed from a start point of a time base, is set as a first similarity calculation area $M_{na}$ and an area in which a predetermined time is retraced from an end point of the time base, is set as a second similarity calculation area $M_{nb}$ with respect to initially-set respective voice data segments $S_n$.

At first and second voice data segments $S_1$ and $S_2$ sequentially arranged along the time base at the voice data segments $S_n$, the similarity between the waveform of voice data in a second similarity calculation area $M_{1b}$ set to the first voice data segment $S_1$ and the waveform of voice data in a first similarity calculation area $M_{2a}$ set to the second voice data segment $S_2$ is calculated. For example, cross-correlation function values for the mutual waveforms are calculated as similarities.

Next, as shown in FIG. 7B, the positions of the respective voice data segments $S_n$ are adjusted.

Here, the above similarities are calculated at the positions where the positions on the time base, of the voice data segments $S_n$ are moved along the time base. The respective voice data segments $S_n$ are moved to the positions where the similarities calculated in its moving range become a maximum value.

When the second voice data segment $S_2$ is moved within a predetermined range along the time base as shown in FIG. 7B for example, the position of the second voice data segment $S_2$ is adjusted to a position shifted from an initial position by a predetermined interval d in such a manner that the similarity between the waveform of voice data in the second similarity calculation area $M_{1b}$ of the first voice data segment $S_1$ and the waveform of voice data in the first similarity calculation area $M_{2a}$ of the second voice data segment $S_2$ becomes a maximum value. This processing is sequentially executed on the respective voice data segments $S_n$ to adjust the positions on the time base, of the voice data segments $S_n$.

Next, as shown in FIG. 7C, for example, the same area as the first similarity calculation area $M_{na}$ set as described above is set as a first overlap area $S_{na}$. For example, the same area as the second similarity calculation area $M_{nb}$ is set as a second overlap area $S_{nb}$.

Thereafter, as shown in FIG. 7D, the first and second overlap areas $S_{na}$ and $S_{nb}$ set as described above are sequentially combined so as to overlap each other along the time base, thereby generating voice playback data DS.

Thus, in the WSOLA method, the waveform of voice data in the second overlap area $S_{nb}$ of each voice data segment $S_n$ and the waveform of voice data in the first overlap area $S_{(n+1)b}$ caused to overlap with its subsequent voice data segment $S_{n+1}$ are made similar to each other and combined together. Therefore, the voice playback data in which the voice data in the overlap areas $S_{nb}$ and $S_{(n+1)b}$ are combined, becomes continuous as compared with the OLA method and the voice is reproduced in the natural musical pitch.

There is however a case in which even in the case where the WSOLA method is applied, the voice playback data is reproduced unnaturally. Since, for example, the value of similarity between the waveform of the voice data in the second overlap area $S_{nb}$ of each voice data segment $S_n$ and the waveform of the voice data in the first overlap area $S_{(n+1)b}$ caused to overlap with its subsequent voice data segment $S_{n+1}$ is small and similarity is poor, the voice might not be reproduced in the natural musical pitch.

Thus, when the voice data is converted to its corresponding voice playback data so as to correspond to the magnification of the playback velocity at the reproduction of the voice data, and the converted voice playback data is reproduced and outputted, the voice playback data becomes discontinuous and the voice quality might be deteriorated as in the case of the reproduction of voice in the unnatural musical pitch and the like.

BRIEF DESCRIPTION OF THE INVENTION

In one aspect, a voice data processing apparatus is provided for converting voice data to voice playback data by an OLA method so as to correspond to a set magnification of playback velocity, including a voice data block setting device which partitions the voice data thereby to set a plurality of voice data blocks, a segment setting device which sets voice data segments to the voice data so as to correspond to the respective voice data blocks set by the voice data block setting device, a segment adjuster which adjusts positions and lengths on a time base, of the voice data segments set by the segment setting device, and a voice playback data generator which combines the respective voice data segments adjusted by the segment adjuster so as to overlap each other along the time base, thereby generating the voice playback data. The segment adjuster includes a similarity calculation area setting device which sets a predetermined area located on the side of a start point on the time base, of each voice data segment set by the segment setting device as a first similarity calculation area and sets a predetermined area located on the side of an end point side on the time base, of the voice data segment as a second similarity calculation area, and a similarity calculation device which calculates similarities between a waveform of voice data in the second similarity calculation area set to a first voice data segment and a waveform of voice data in the first similarity calculation area set to a second voice data segment with respect to the first and second voice data segments arranged sequentially along the time base, of the voice data segments in which the first and second similarity calculation areas have been set by the similarity calculation area setting device. In a range in which the start and end points on the time base, of the voice data segments are respectively moved along the time base, the positions and lengths on the time base, of the voice data segments are adjusted based on the similarities calculated by the similarity calculation device.

In another aspect, a voice data processing method is provided for converting voice data to voice playback data by an OLA method so as to correspond to a set magnification of playback velocity, including the steps: a voice data block setting step for partitioning the voice data thereby to set a plurality of voice data blocks, a segment setting step for setting voice data segments to the voice data so as to correspond to the respective voice data blocks set by the voice data block setting step, a segment adjusting step for adjusting positions and lengths on a time base, of the voice data segments set by the segment setting step, and a voice playback data generating step for combining the respective voice data segments adjusted by the segment adjusting step so as to overlap each other along the time base, thereby generating the voice playback data. The segment adjusting step includes a similarity calculation area setting step for setting a predetermined area located on the side of a start point on the time base, of each voice data segment set by the segment setting step as a first similarity calculation area and setting a predetermined area located on the side of an end point side on the time base, of the voice data segment as a second similarity calculation area, and a similarity calculating step for calculating similarities between a waveform of voice data in the second similarity calculation area set to a first voice data segment and a waveform of voice data in the first similarity calculation area set to a second voice data segment with respect to the first and second voice data segments arranged sequentially along the time base, of the voice data segments in which the first and second similarity calculation areas have been set by the similarity calculation area setting step. In a range in which the start and end points on the time base, of the voice data segments are respectively moved along the time base, the positions and lengths on the time base, of the voice data segments are adjusted based on the similarities calculated by the similarity calculating step.

In another aspect, an imaging apparatus is provided for executing scans on an imaging area of a subject thereby to image the imaging area of the subject, including a voice data processing unit which converts voice data to voice playback data by an OLA method so as to correspond to a set magnification of playback velocity, and a voice information provision unit which outputs the voice playback data converted by the voice data processing unit thereby to provide voice information to the subject. The voice data processing unit includes a voice data block setting device which partitions the voice data thereby to set a plurality of voice data blocks, a segment setting device which sets voice data segments to the voice data so as to correspond to the respective voice data blocks set by the voice data block setting device, a segment adjuster which adjusts positions and lengths on a time base, of the voice data segments set by the segment setting device, and a voice playback data generator which combines the respective voice data segments adjusted by the segment adjuster so as to overlap each other along the time base, thereby generating the voice playback data. The segment adjuster includes a similarity calculation area setting device which sets a predetermined area located on the side of a start point on the time base, of each voice data segment set by the segment setting device as a first similarity calculation area and sets a predetermined area located on the side of an end point side on the time base, of the voice data segment as a second similarity calculation area, and a similarity calculation device which calculates similarities between a waveform of voice data in the second similarity calculation area set to a first voice data segment and a waveform of voice data in the first similarity calculation area set to a second voice data segment with respect to the first and second voice data segments arranged sequentially along the time base, of the voice data segments in which the first and second similarity calculation areas have been set by the similarity calculation area setting device. In a range in which the start and end points on the time base, of the voice data segments are respectively moved along the time base, the positions and lengths on the time base, of the voice data segments are adjusted based on the similarities calculated by the similarity calculation device.

Embodiments described herein provide a voice data processing apparatus, a voice data processing method and an imaging apparatus respectively capable of improving the quality of voice to be reproduced when a playback velocity of the voice is changed.

BRIEF DESCRIPTION OF THE DRAWINGS

FIGS. 4A through 4I are diagrams illustrating the contents of the data processing executed when the voice information is provided to the subject upon imaging of the photographing area of the subject using the magnetic resonance imaging apparatus shown in FIG. 1.

FIG. 5 is a diagram showing a plurality of similarities calculated about two voice data segments sequentially arranged along a time base at a plurality of voice data segments.

FIGS. 7A through 7D are diagrams illustrating data processing for converting voice data to voice playback data so as to correspond to a magnification of a playback velocity used to reproduce the voice data by a WSOLA method.

DETAILED DESCRIPTION OF THE INVENTION

Figure 1:
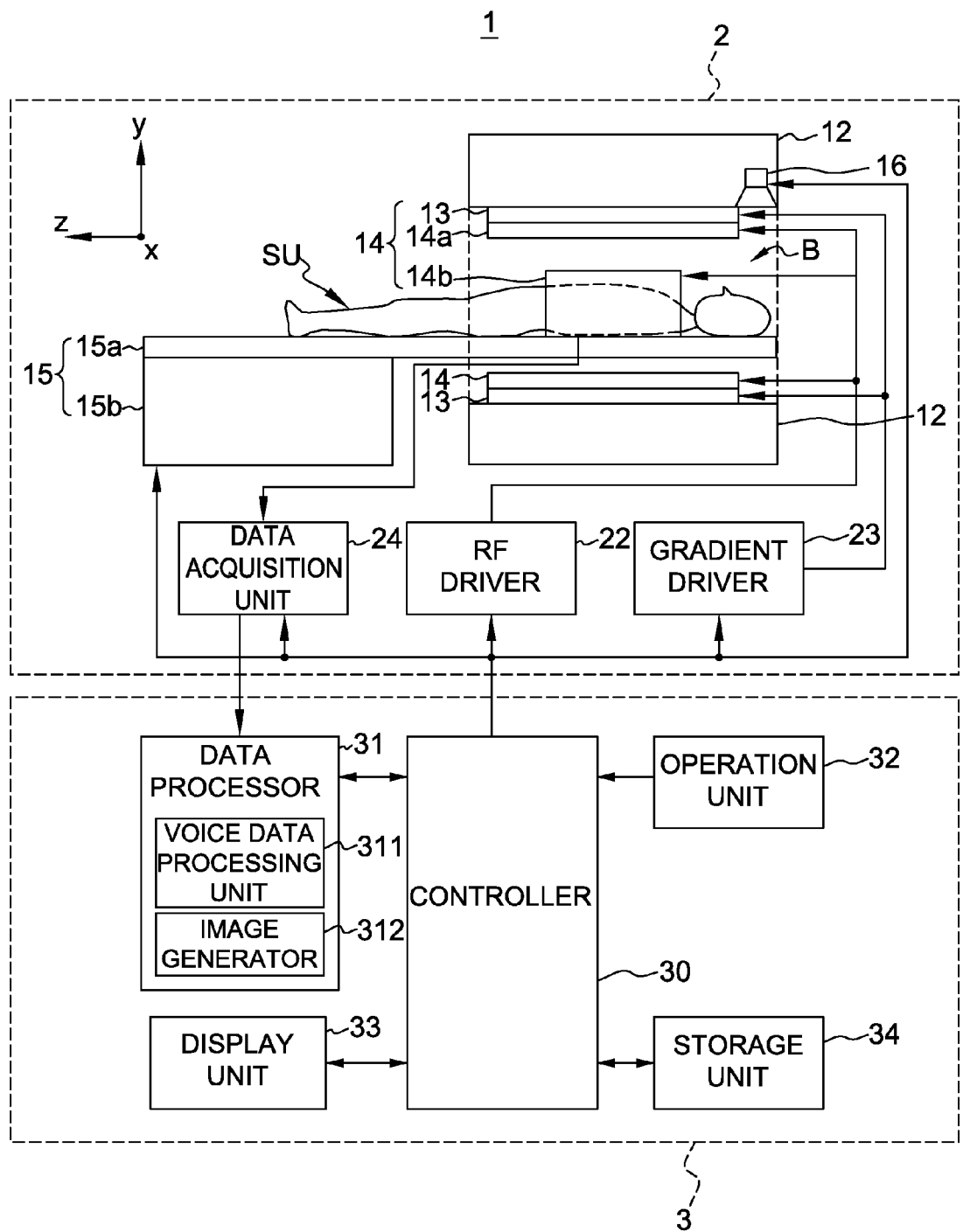
FIG. 1 is a configuration diagram showing a construction of an exemplary magnetic resonance imaging apparatus.

FIG. 1 is a configuration diagram showing a construction of an exemplary magnetic resonance imaging apparatus 1.

As shown in FIG. 1, the magnetic resonance imaging apparatus 1 has a scan section 2 and an operation console section 3. Here, the scan section 2 has a static magnetic field magnet unit 12, a gradient coil unit 13, an RF coil unit 14, a subject movement unit 15, a voice information provision unit 16, an RF driver 22, a gradient driver 23 and a data acquisition unit 24 as shown in FIG. 1. As shown in FIG. 1, the operation console section 3 has a controller 30, a data processor 31, an operation unit 32, a display unit 33 and a storage unit 34. The data processor 31 has a voice data processing unit 311 and an image generator 312.

The scan section 2 will be explained.

The scan section 2 executes a scan on an imaging area of a subject SU, based on a control signal outputted from the operation console section 3. Here, the scan section 2 is formed so as to assume or take a cylindrical shape, for example and holds or accommodates therein the subject SU with a columnar space at its central part as an imaging space B. When the scan section 2 scans the imaging area of the subject SU, the RF coil unit 14 transmits an RF pulse so as to excite spins in the imaging area of the subject SU placed on the subject movement unit 15 within the imaging space B formed with a static magnetic field by the static magnetic field magnet unit 12. Further, the gradient coil unit 13 applies a gradient magnetic field to the imaging area of the subject SU to which the RF pulse is transmitted. The RF coil unit 14 receives each magnetic resonance signal generated at the imaging area of the subject SU.

Respective constituent elements of the scan section 2 will be explained sequentially.

The static magnetic field magnet unit 12 includes a superconductive magnet (not shown) and forms a static magnetic field in the imaging space B in which the subject SU is accommodated or held. Here, the static magnetic field magnet unit 12 forms the static magnetic field so as to extend along a body-axis direction (z direction) of the subject SU placed on the subject movement unit 15. That is, the static magnetic field magnet unit 12 is of a horizontal magnetic field type. In addition to it, the static magnetic field magnet unit 12 may be one that is of a vertical magnetic field type and forms a static magnetic field along the direction in which a pair of permanent magnets faces each other.

The gradient coil unit 13 forms a gradient magnetic field in the imaging space B formed with the static magnetic field by the static magnetic field magnet unit 12 and applies or adds spatial position information to each magnetic resonance signal received by the RF coil unit 14. Here, the gradient coil unit 13 includes three systems so as to correspond to three-axis directions of an x direction, a y direction and a z direction orthogonal to one another. These transmit gradient pulses in a frequency encode direction, a phase encode direction and a slice selection direction according to imaging conditions respectively so as to form gradient magnetic fields. Described specifically, the gradient coil unit 13 applies the gradient magnetic field in the slice selection direction of the subject SU and selects a slice of the subject SU excited by transmission of an RF pulse by the RF coil unit 14. The gradient coil unit 13 applies the gradient magnetic field in the phase encode direction of the subject SU and phase-encodes a magnetic resonance signal from the slice excited by the RF pulse. And the gradient coil unit 13 applies the gradient magnetic field in the frequency encode direction of the subject SU and frequency-encodes the magnetic resonance signal from the slice excited by the RF pulse.

The RF coil unit 14 transmits an RF pulse corresponding to an electromagnetic wave to the imaging area of the subject SU within the imaging space B formed with the static magnetic field to form a high frequency magnetic field, thereby exciting the spins of proton in the imaging area of the subject SU. The RF coil unit 14 receives an electromagnetic wave generated from the excited proton in the imaging area of the subject SU as a magnetic resonance signal. For example, the RF coil unit 14 has a transmitting coil 14a and a receiving coil 14b as shown in FIG. 1. Here, the transmitting coil 14a is of, for example, a birdcage type body coil, which is disposed so as to surround the imaging area of the subject SU and transmits an RF pulse. On the other hand, the receiving coil 14b is of a surface coil, which receives each magnetic resonance signal.

The subject movement unit 15 has a cradle 15a and a cradle moving part 15b as shown in FIG. 1. The subject movement unit 15 is configured in such a manner that the cradle moving part 15b moves the cradle 15a between the inside and outside of the imaging space B based on a control signal outputted from the operation console section 3. Here, the cradle 15a is a table that includes a placement surface on which the subject SU is placed. As shown in FIG. 1, the cradle 15a is moved in a horizontal direction xz and a vertical direction y by the cradle moving part 15b and carried in and out from the imaging space B formed with the static magnetic field. The cradle moving part 15b moves the cradle 15a and allows it to be accommodated inside the imaging space B from outside. The cradle moving part 15b is provided with, for example, a roller type drive mechanism, which drives a roller by an actuator to move the cradle 15a in the horizontal direction xz. The cradle moving part 15b is provided with, for example, an arm type drive mechanism, which varies the angle formed between two arms that intersect each other, thereby moving the cradle 15a in the vertical direction y.

The voice information provision unit 16 includes a speaker and outputs voice from the speaker thereby to provide voice information for the subject SU. In the present embodiment, the voice information provision unit 16 provides voice information for the subject SU, based on voice playback data outputted after conversion of voice data by the voice data processing unit 311 of the data processor 31. In the present embodiment, the voice information provision unit 16 provides the voice information for the subject SU upon scanning the subject SU.

The RF driver 22 drives the RF coil unit 14 to transmit an RF pulse to within the imaging space B, thereby forming a high frequency magnetic field in the imaging space B. Described specifically, the RF driver 22 modulates a signal sent from an RF oscillator (not shown) to a signal having predetermined timing and predetermined envelope using a gate modulator (not shown) on the basis of a control signal outputted from the operation console section 3. Thereafter, the RF driver 22 allows an RF power amplifier (not shown) to amplify the signal modulated by the gate modulator and outputs the same to the RF coil unit 14, and allows the RF coil unit 14 to transmit the corresponding RF pulse.

The gradient driver 23 applies a gradient pulse to the gradient coil unit 13 based on the corresponding control signal from the operation console section 3 to drive the gradient coil unit 13, thereby forming a gradient magnetic field within the imaging space B formed with the static magnetic field. Here, the gradient driver 23 has drive circuits of three systems (not shown) in association with the three-system gradient coil unit 13.

The data acquisition unit 24 collects or acquires the magnetic resonance signals received by the RF coil unit 14, based on the corresponding control signal sent from the operation console section 3. Here, the data acquisition unit 24 phase-detects each magnetic resonance signal received by the RF coil unit 14 by a phase detector (not shown) with the output of the RF oscillator (not shown) of the RF driver 22 as a reference signal. Thereafter, an A/D converter (not shown) is used to convert the magnetic resonance signal corresponding to this analog signal to a digital signal and outputs the same therefrom.

The operation console section 3 will be explained.

The operation console section 3 controls the scan section 2 in such a manner that the scan section 2 executes scans for the imaging area of the subject SU. The operation console section 3 generates a magnetic resonance image for the imaging area of the subject SU, based on the magnetic resonance signals acquired by executing the scans by means of the scan section 2 and displays the generated magnetic resonance image.

Respective constituent elements or components of the operation console section 3 will be described sequentially.

The controller 30 has a computer and a memory that stores therein a program for allowing the computer to execute predetermined data processing and controls the respective parts. Here, the controller 30 outputs control signals to the subject movement unit 15, the voice information provision unit 16, the RF driver 22, the gradient driver 23 and the data acquisition unit 24 based on operation data inputted to the operation unit 32 by an operator thereby to allow them to execute scans. Along with it, the controller 30 outputs control signals to the data processor 31, the display unit 33 and the storage unit 34 to control them.

The data processor 31 has a computer and a memory that stores therein a program for executing predetermined data processing using the computer. The data processor 31 executes data processing, based on the corresponding control signal outputted from the controller 30. Here, as shown in FIG. 1, the data processor 31 has the voice data processing unit 311 and the image generator 312 and is configured in such a manner that the computer functions as each part referred to above according to the program.

The voice data processing unit 311 of the data processor 31 outputs the stored voice data to the voice information provision unit 16 provided in the scan section 2 as shown in FIG. 1 as voice playback data, thereby reproducing voice and providing voice information to the subject SU. In the present embodiment, the voice data processing unit 311 performs data processing for converting voice data to voice playback data by an OLA method so as to correspond to a magnification of a playback or reproduction rate or velocity inputted and set to the operation unit 32 by the operator. Here, the voice data processing unit 311 converts the voice data to the voice playback data in association with the playback velocity at which the reproduction of the voice playback data is completed between the time prior to the start of the scan for the subject SU and the time when the scan is started.

Figure 2:
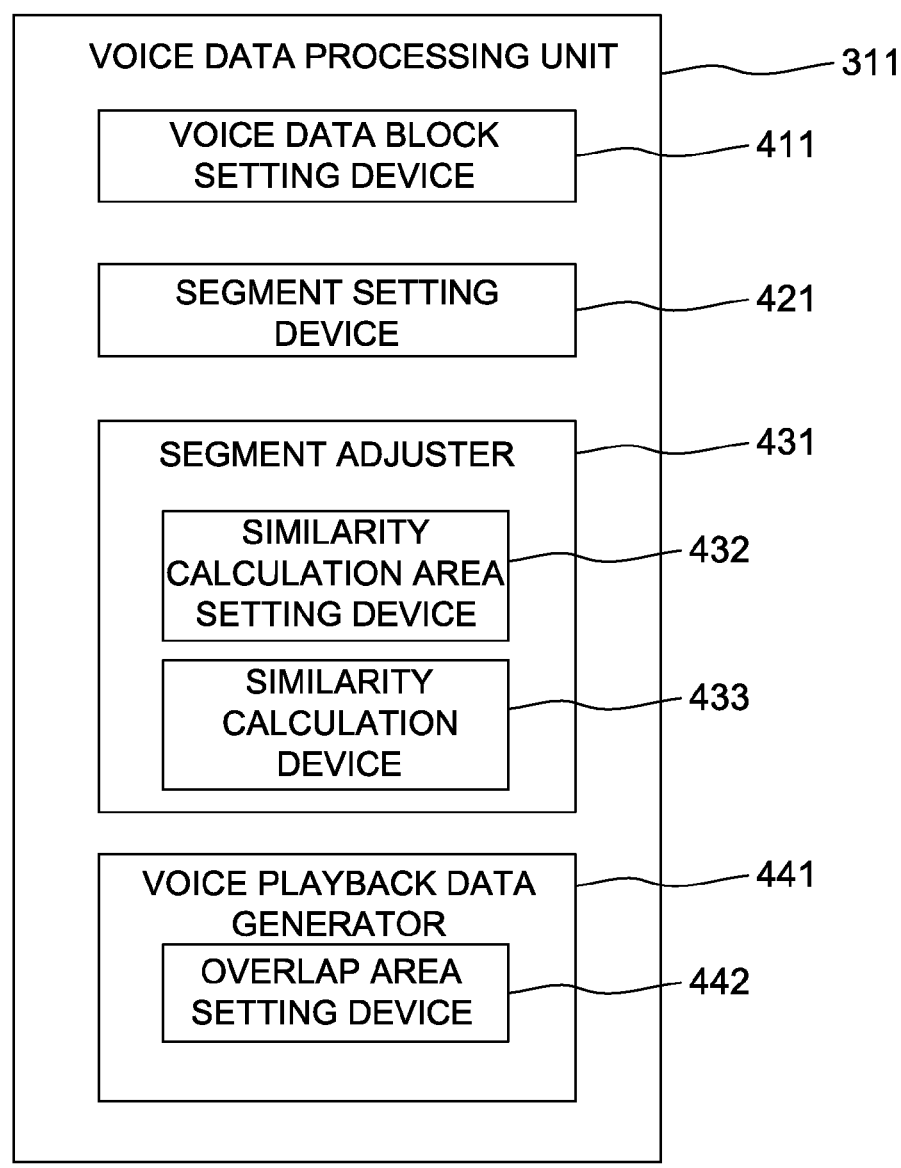
FIG. 2 is a functional block diagram showing an exemplary voice data processing unit that may be used with the magnetic resonance imaging apparatus shown in FIG. 1.

FIG. 2 is a functional block diagram showing the voice data processing unit 311 employed in the embodiment according to the invention.

The voice data processing unit 311 has a voice data block setting device 411, a segment setting device 421, a segment adjuster 431 and a voice playback data generator 441 as shown in FIG. 2.

The voice data block setting device 411 of the voice data processing unit 311 sections or partitions voice data inputted as a digital signal at equal time intervals thereby to set a plurality of voice data blocks.

The segment setting device 421 of the voice data processing unit 311 sets voice data segments to the voice data so as to correspond to the respective voice data blocks set by the voice data block setting device 411.

The segment adjuster 431 of the voice data processing unit 311 adjusts the positions and lengths on a time base, of the respective voice data segments set by the segment setting device 421.

In the present embodiment, the segment adjuster 431 has a similarity calculation area setting device 432 and a similarity calculation device 433 as shown in FIG. 2.

Here, the similarity calculation area setting device 432 in the segment adjuster 431 sets a predetermined area positioned on the start-point side on the time base, of each voice data segment set by the segment setting device 421 as a first similarity calculation area and sets a predetermined area located on the end-point side on the time base, of each voice data segment as a second similarity calculation area.

The similarity calculation device 433 in the segment adjuster 431 calculates similarities between the waveform of voice data in the second similarity calculation area set to the first voice data segment and the waveform of voice data in the first similarity calculation area set to the second voice data segment with respect to the first and second voice data segments arranged sequentially along the time base, of the voice data segments in which the first and second similarity calculation areas have been set by the similarity calculation area setting device 432.

In the present embodiment, the similarity calculation device 433 calculates cross-correlation functions of the waveform of the voice data in the second similarity calculation area set to the first voice data segment and the waveform of the voice data in the first similarity calculation area set to the second voice data segment as similarities.

The segment adjuster 431 adjusts the positions and lengths on the time base, of the voice data segments, based on the similarities calculated by the similarity calculation device 433 in a range in which the start and end points of the time base for the voice data segments are respectively moved along the time base. In the present embodiment, as will be described later in detail, the segment adjuster 431 adjusts the positions and lengths on the time base, of the voice data segments in such a manner that the corresponding similarity calculated by the similarity calculation device becomes a maximum value in the range in which the start and end points on the time base, of each voice data segment are respectively moved along the time base.

The voice playback data generator 441 of the voice data processor 311 combines the respective voice data segments adjusted by the segment adjuster 431 with being overlapped each other along the time base, thereby to generate voice playback data.

In the present embodiment, the voice playback data generator 441 includes an overlap area setting device 442 as shown in FIG. 2.

Here, the overlap area setting device 442 in the voice playback data generator 441 sets an area in which a predetermined time interval has elapsed since the start point of the time base at each of the voice data segments adjusted by the segment adjuster 431, as a first overlap area, and sets an area in which a predetermined time interval is retraced from the end point of the time base at each voice data segment, as a second overlap area. In the present embodiment, the overlap area setting device 442 sets the first similarity calculation area set by the similarity calculation area setting device 432 as the first overlap area and sets the second similarity calculation area set by the similarity calculation area setting device 432 as the second overlap area.

The voice playback data generator 441 combines the second overlap area set to the first voice data segment by the overlap area setting device 442 and the first overlap area set to the second voice data segment so as to overlap each other with respect to the first and second voice data segments sequentially arranged along the time base at the voice data segments adjusted by the segment adjuster 431, thereby generating the voice playback data.

The image generator 312 of the data processor 31 uses the magnetic resonance signals acquired by causing the scan section 2 to execute scans, as raw data and thereby generates a magnetic resonance image for the subject SU. Described specifically, the image generator 312 acquires each of the magnetic resonance signals acquired by the data acquisition unit 24 by execution of the scans as a digital signal and performs image reconstruction processing on each magnetic resonance signal converted to the digital signal, thereby generating a magnetic resonance image about a slice area of the subject SU. For example, the image generator 312 inversely Fourier-transforms each of magnetic resonance signals acquired corresponding to a k space thereby to reconstruct a magnetic resonance image. The image generator 312 outputs image data about the generated magnetic resonance image to the display unit 33.

The operation unit 32 is constituted of operation devices such as a keyboard, a pointing device and the like. The operation unit 32 inputs operation data from the operator and outputs the same to the controller 30.

The display unit 33 is constituted of a display device such as an LCD (Liquid Crystal Display), a CRT or the like and displays each image on its display screen, based on the control signal outputted from the controller 30. For example, the display unit 33 displays operation images indicative of input items corresponding to the operation data inputted to the operation unit 32 by the operator on the display screen prior to the execution of each scan. After the scan execution, the display unit 33 displays a magnetic resonance image generated at the data processor 31, based on the magnetic resonance signals acquired by the execution of the scans on the display screen.

The storage unit 34 includes a memory and stores various data therein. In the storage unit 34, the data stored therein are accessed by the controller 30 as needed.

Operation

The operation of the magnetic resonance imaging apparatus 1 (shown in FIG. 1) will be explained below.

The present embodiment will explain the operation of changing a magnification of a reproduction or playback velocity of voice data so as to match voice data indicating that a subject SU is caused to stop breathing to prevent the occurrence of body motion due to the breathing operation of the subject SU, with timing provided to execute each scan and thereby reproducing and outputting the voice data automatically prior to the start of the scan.

Figure 3:
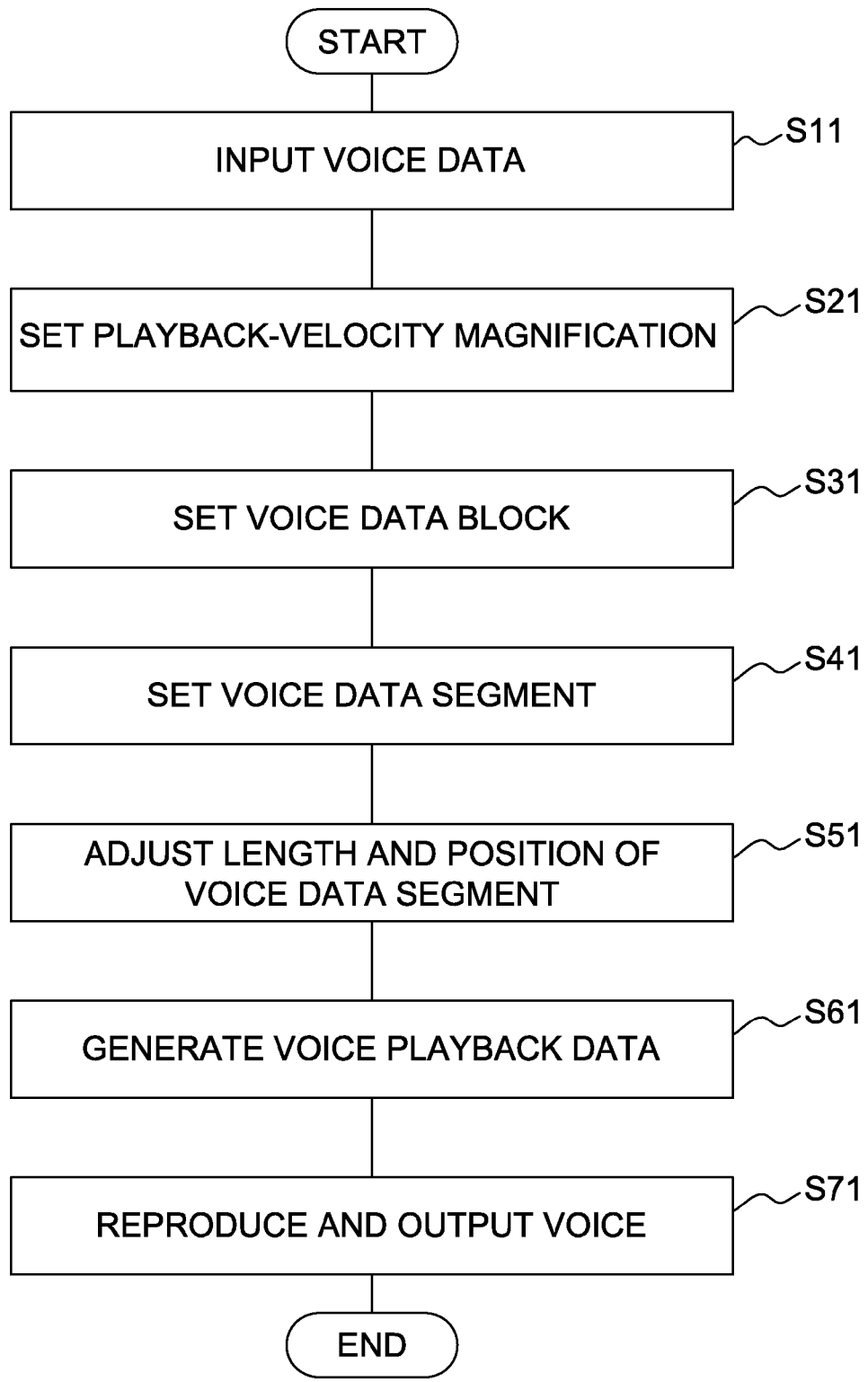
FIG. 3 is a flowchart illustrating an exemplary data processing method executed when voice information is provided to a subject upon imaging of a photographing area of the subject using the magnetic resonance imaging apparatus shown in FIG. 1.

FIG. 3 is a flowchart showing data processing executed when voice information is provided to a subject SU upon imaging of a photographing or imaging area of the subject SU in the embodiment according to the invention. FIGS. 4A through 4I are diagrams illustrating the contents of the data processing executed when the voice information is provided to the subject SU upon imaging of the photographing area of the subject SU in the embodiment according to the invention.

When voice is reproduced and outputted, the input of voice data is first executed as shown in FIG. 3 (S11).

Figure 4A:
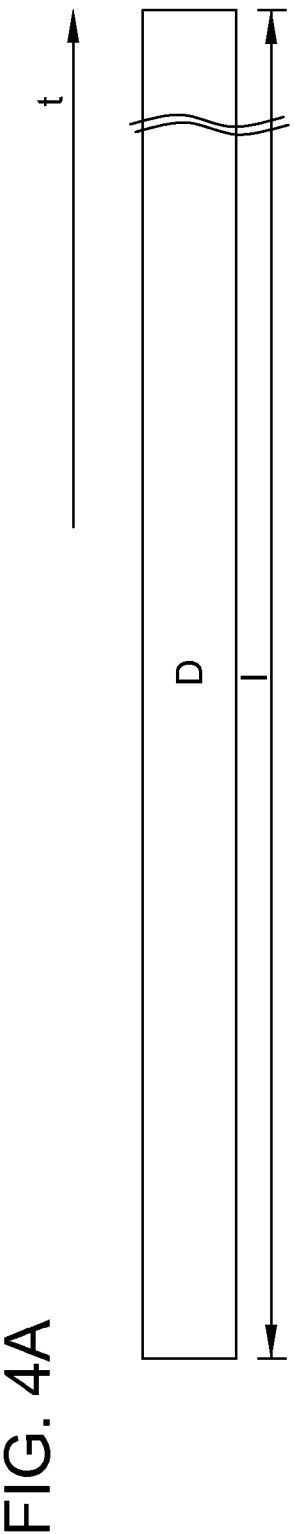

Here, as shown in FIG. 4A, voice data D at which the time taken to reproduce it at a reference velocity becomes a predetermined reproduction or playback time I, is inputted from the storage unit 34 to the voice data processing unit 311. For example, voice data D indicative of respiration guide information such as "Please stop your breathing" is inputted thereto.

Next, the setting of a playback-velocity magnification is executed as shown in FIG. 3 (S21).

Here, the setting of the playback-velocity magnification V is performed in such a manner that the voice data D at which the time taken to reproduce it at the reference velocity reaches the predetermined playback time I is reproduced during a desired reproduction or playback time Ie.

For example, the time taken until a contrast agent is injected into the blood flowing in a subject and the injected contrast agent reaches an imaging area in which the subject is imaged, is calculated as the playback time Ie. The playback-velocity magnification V of the voice data D is set in such a manner that the voice data D is reproduced during the calculated playback time Ie.

Described concretely, the voice data processing unit 311 executes data processing so as to divide the desired playback time Ie by the predetermined playback time I corresponding to the time provided for the reproduction at the reference velocity, thereby calculating and setting the playback-velocity magnification V.

Next, voice data blocks are set as shown in FIG. 3 (S31).

Figure 4B:
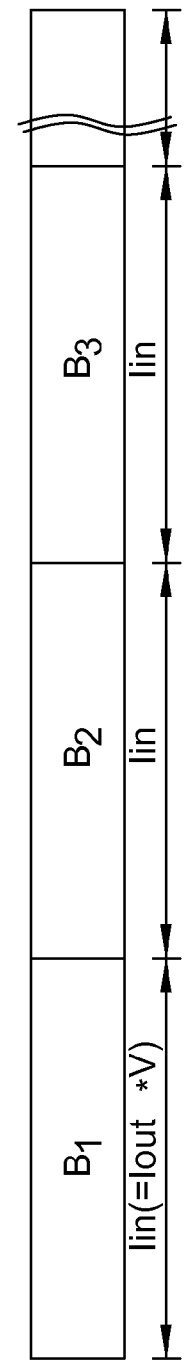

Here, as shown in FIG. 4B, the voice data block setting device 411 of the voice data processing unit 311 partitions the voice data D inputted as a digital signal at equal time intervals thereby to set the same to a plurality of voice data blocks $B_n$ (where n=1, 2, ..., i) (where i: integer)).

Described concretely, the voice data D is divided at the equal time intervals based on the OLA method in such a manner that lengths (time intervals) Iin on a time base t become identical to each other at the voice data blocks $B_n$. Here, as mentioned above, the lengths Iin of the voice data D are defined in such a manner that the lengths Iin become a value obtained by multiplying the playback-velocity magnification V by a predetermined value Iout. The lengths thereof are partitioned sequentially from the start point of the voice data D. For example, the predetermined value Iout is assumed to be 90 ms and the length Iin of each voice data block $B_n$ is assumed to be 180 ms when the playback velocity is set to a playback velocity equal to twice the reference velocity.

As shown in FIG. 4B by way of example, a range from the start point of the time base t for the voice data D to the point of time at which a predetermined time interval Iin is spaced away therefrom is partitioned as a first voice data block $B_1$. A range from the end point of the time base for the first voice data block $B_1$ to the point of time at which the predetermined time interval Iin is spaced away therefrom is partitioned as a second voice data block $B_2$. Further, a range from the end point of the time base t for the second voice data block $B_2$ to the point of time at which the predetermined time interval Iin is spaced away therefrom is partitioned as a third voice data block $B_3$.

Next, the setting of voice data segments is executed as shown in FIG. 3 (S41).

Figure 4C:
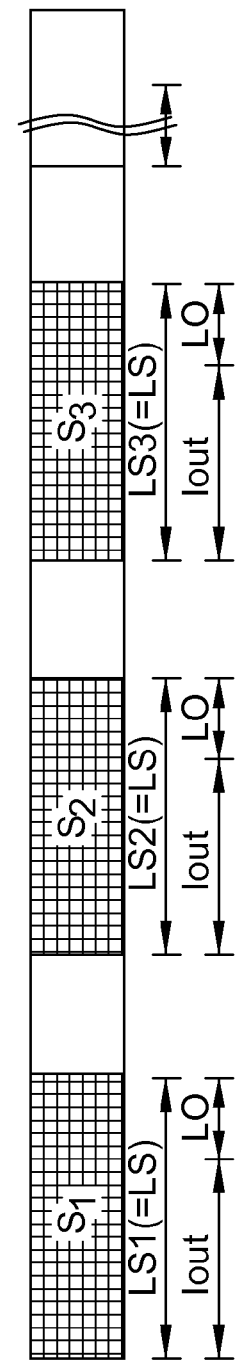

Here, the segment setting device 421 of the voice data processing unit 311 sets a plurality of voice data segments $S_n$ (where n=1, 2, ..., i) (where i: integer) to the voice data D so as to correspond to the set voice data blocks $B_n$ as shown in FIG. 4C.

Described concretely, the respective voice data segments $S_n$ are defined in such a manner that the start point of the time base t for each voice data segment $S_n$ corresponds to the start point of the time base t for each voice data block $B_n$, and the lengths LS on the time base t become identical. Here, the value obtained by adding the length LO of each of overlap areas $S_{na}$ and $S_{nb}$ to be described later to a predetermined value Iout is set as the length LS of each voice data segment $S_n$ in a manner similar to the OLA method. Assuming that for example, the predetermined value Iout is 90 ms and the length LO of each of the overlap areas $S_{na}$ and $S_{nb}$ is 10 ms as described above, the length LS of each voice data segment $S_n$ is set as 100 ms.

As shown in FIG. 4C, for example, a range from the start point of the time base t for first voice data block $B_1$ to the point of time at which a predetermined time interval LS is spaced away therefrom, is defined as a first voice data segment $S_1$. A range from the start point of the time base t for the second voice data block $B_2$ to the point of time at which the predetermined time interval LS is spaced away therefrom, is defined as a second voice data segment $S_2$. A range from the start point of the time base t for the third voice data block $B_3$ to the point of time at which the predetermined time interval LS is spaced away therefrom, is defined as a third voice data segment $S_3$.

Next, adjustments to the lengths and positions of the voice data segments are carried out as shown in FIG. 3 (S51).

Here, the segment adjuster 431 of the voice data processing unit 311 adjusts the positions and lengths on the time base, of the respective voice data segments Sn set in the above-described manner.

Described concretely, as shown in FIG. 4D, the similarity calculation area setting device 432 of the segment adjuster 431 first sets an area in which a predetermined time has elapsed from the start point of the time base, as a first similarity calculation area $M_{na}$ and sets an area in which a predetermined time is retraced from the end point of the time base, as a second similarity calculation area $M_{nb}$ with respect to the respective voice data segments $S_n$ set by the above in a manner similar to the WSOLA method.

At two voice data segments $S_n$ and $S_{n+1}$ sequentially arranged along the time base in the plural voice data segments Sn, the similarity calculation device 433 executes the process of calculating similarities between the waveform of voice data of a second similarity calculation area $M_{nb}$ set to the previous voice data segment $S_n$ and the waveform of voice data of a first similarity calculation area $M_{(n+1)a}$ set to the subsequent voice data segment $S_{n+1}$.

For example, cross-correlation function values of the waveform of the voice data of the second similarity calculation area $M_{nb}$ set to the previous voice data segment $S_n$ and the waveform of the voice data of the first similarity calculation area $M_{(n+1)a}$ set to the second voice data segment $S_{(n+1)a}$ are calculated as similarities.

In the present embodiment, the above similarities are calculated in the range in which the lengths and positions on the time base, of the respective voice data segments $S_n$. Namely, unlike the WSOLA method, the lengths on the time base, of the voice data segments $S_n$ are varied as well as the positions on the time base, of the voice data segments $S_n$, and the similarities are calculated at the varied positions.

Described concretely, at the two voice data segments $S_n$ and $S_{n+1}$ arranged sequentially along the time base, the position of the end point of the previous voice data segment $S_n$ is sequentially shifted from an initial position $P_{nc}$ every predetermined interval d, and the position of the start point of the subsequent voice data segment $S_{n+1}$ is sequentially shifted from an initial position $P_{(n+1)s}$ for every predetermined intervals d, thereby sequentially calculating similarities related to their combinations.

As shown in FIG. 4D for example, a position $P_{1e}$ of an end point of a first voice data segment $S_1$ is shifted from an initial position (0) for every predetermined interval (+d, +2d) so as to approach a subsequent second voice data segment $S_2$ and shifted for every predetermined interval (−d, −2d) so as to move away from the second voice data segment $S_2$. A position $P_{2s}$ of a start point of the second voice data segment $S_2$ is shifted from an initial position for every predetermined interval (−d, −2d) so as to approach the previous first voice data segment $S_1$ and shifted for every predetermined interval (+d, +2d) so as to move away from the first voice data segment $S_1$. A plurality of similarities are calculated so as to correspond to respective combinations of the cases where the voice data segments are shifted to the positions respectively.

FIG. 5 is a diagram showing a plurality of similarities calculated about two voice data segments sequentially arranged along a time base at a plurality of voice data segments in the embodiment according to the invention.

As shown in FIG. 5, for example, a position $P_{ne}$ of an end point of a previous voice data segment $S_n$ is sequentially shifted from an initial position (0) every predetermined interval (d1=−2d, −d, 0, +d, +2d), and a position $P_{(n+1)s}$ of a start point of a subsequent voice data segment $S_{n+1}$ is sequentially shifted from an initial position (0) every predetermined interval (d2=−2d, −d, 0, +d, +2d), thereby sequentially calculating similarities $S_m$ (d1, d2) related to their combinations. Namely, as shown in FIG. 8, the similarities $S_m$ (d1, d2) are sequentially calculated to fill in respective matrices defined by the position $P_{ne}$ of the end point of the previous voice data segment $S_n$ and the position $P_{(n+1)s}$ of the start point of the subsequent voice data segment $S_{n+1}$.

In the table shown in FIG. 5, for example, a plurality of similarities Sm (−2d, −2d), Sm (−2d, −d), Sm (−2d, 0), Sm (−2d, +d) and Sm (−2d, +2d) arranged in a first row are sequentially calculated. Thereafter, a plurality of similarities Sm (−d, −2d), Sm (−d, −d), Sm (−d, 0), Sm (−d, +d) and Sm (−d, +2d) arranged in a second row are sequentially calculated. Likewise, similarities Sm (d1, d2) arranged in row directions in order of a third row, a fourth row and a fifth row are sequentially calculated.

The segment adjuster 431 adjusts the lengths and positions of the respective voice data segments $S_n$ in such a manner that the similarities Sm (d1, d2) calculated in the range in which the lengths and positions on the time base, of the voice data segments $S_n$ are varied as described above are respectively brought to a maximum value.

When the similarity Sm (+d, −d) calculated where as indicated with being surrounded by a thick solid line in FIG. 5, for example, an end point of a first voice data segment $S_1$ is shifted from an initial position to a second voice data segment $S_2$ by a predetermined interval (+d) to bring the first voice data segment $S_1$ to a time interval (LS+d) longer than an initial length thereof, and a start point of the second voice data segment $S_2$ is shifted from an initial position thereof to the first voice data segment $S_1$ by a predetermined interval (−d), is brought to a maximum value, the length of the first voice data segment $S_1$ and the position of the second voice data segment $S_2$ are adjusted so as to correspond to positions thereof as shown in FIG. 4E.

Namely, as shown in FIG. 4E, the position $P_{1e}$ of the end point of the first voice data segment $S_1$ is shifted from the initial position (0) so as to correspond to the determined interval (+d), thereby adjusting the length of the first voice data segment $S_1$ to the length (LS+d) longer than the initial length LS. Further, the position $P_{2s}$ of the start point of the second voice data segment $S_2$ is shifted from the initial position (0) so as to correspond to the determined position (−d), thereby adjusting the position of the second voice data segment $S_2$.

After the similarities between the first voice data segment S1 and the second voice data segment S2 have been calculated in the above-described manner, each similarity between two voice data segments arranged along the time base t is then calculated in a manner similar to the above.

Here, when the average value of the length of the previous voice data segment $S_n$ at the two voice data segments $S_n$ and $S_{n-1}$ arranged along the time base t at which the data processing has been executed as described above, is varied so as to reach from the initial length LS to another length, the length of the previous voice data segment $S_{n+1}$ in two voice data segments $S_{n+1}$ and $S_{n+2}$ arranged along the time base t is adjusted so as to be subtracted from the varied length in the above-described manner.

In the above data processing, if described concretely, the length LS1 of the previously-located first voice data segment $S_1$ in the first and second voice data segments $S_1$ and $S_2$ arranged along the time base t is adjusted so as to vary from the average value LS of the initial length to another length (LS+d). Therefore, the length LS2 of the previously-located second voice data segment $S_2$ is adjusted so as to reach a length (LS−d) obtained by subtracting the varied length d from the initial length LS at the third voice data segment $S_3$ inclusive of the second voice data segment $S_2$ both arranged along the time base t, following the first and second voice data segments $S_1$ and $S_2$ as shown in FIG. 4F.

Similarities between the second voice data segment $S_2$ and the third voice data segment $S_3$ are calculated in a manner similar to the calculation of the similarities between the first and second voice data segments $S_1$ and $S_2$.

Figure 4F:
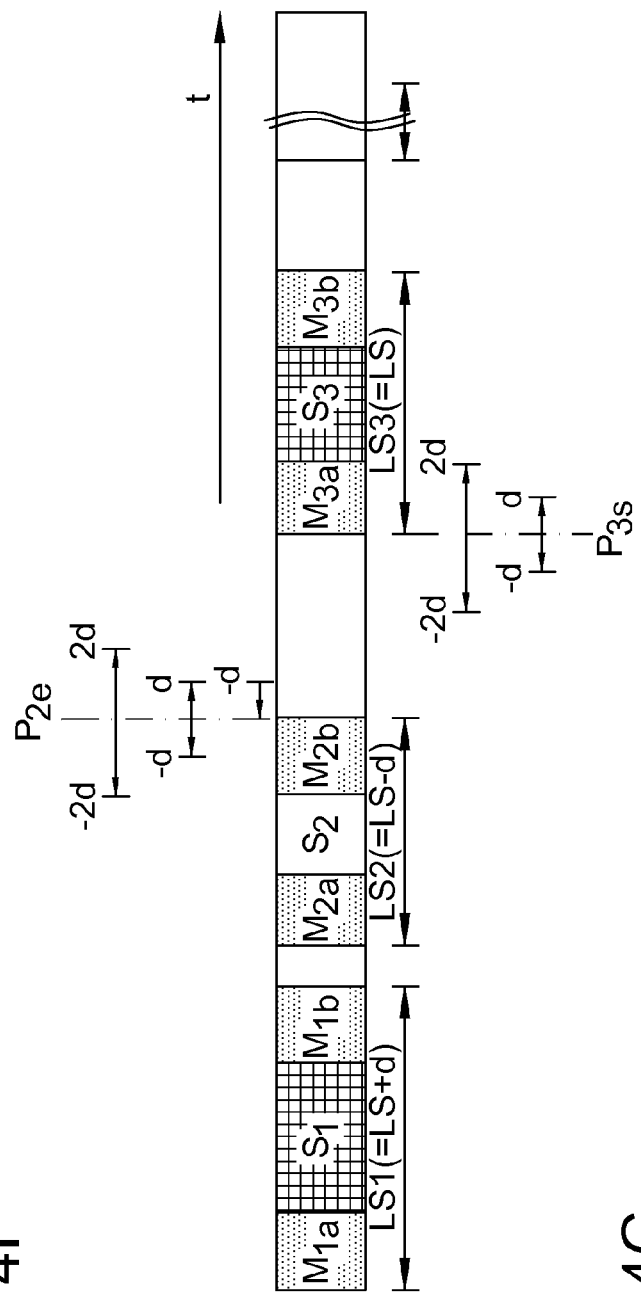

That is, as shown in FIG. 4F, the position $P_{2e}$ of the end point of the second voice data segment $S_2$ is sequentially shifted from its initial position (0) for every predetermined interval (d1=−2d, −d, 0, +d, +2d), and the position $P_{3s}$ of the start point of the third voice data segment $S_3$ located after the second voice data segment $S_2$ is sequentially shifted from its initial position (0) for every predetermined interval (d2=−2d, −d, 0, +d, +2d), thereby sequentially calculating similarities Sm (d1, d2) related to their combinations.

At a plurality of similarities Sm (d1, d2) calculated in a range in which the length of the second voice data segment $S_2$ and the length of the third voice data segment $S_3$ are varied, the length of the second voice data segment $S_2$ at which the similarity Sm (d1, d2) becomes a maximum value, and the position of the third voice data segment $S_3$ are extracted, and the length of the second voice data segment $S_2$ and the position of the third voice data segment $S_3$ are adjusted so as to reach the extracted length and position in a manner similar to the above.

Figure 4G:
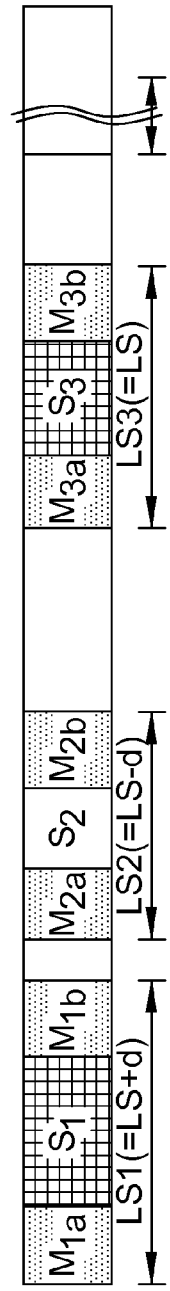

When, for example, the similarity Sm (0, 0) calculated where the end point of the second voice data segment $S_2$ and the start point of the third voice data segment $S_3$ are of the initial position (0), becomes a maximum value, the length of the second voice data segment $S_2$ and the position of the third voice data segment $S_3$ are adjusted so as to be held as shown in FIG. 4G.

By repeating such data processing, adjustments to the lengths and positions of the respective voice data segments $S_n$ are performed.

Next, the generation of voice playback data is carried out as shown in FIG. 3 (S61).

Here, the respective voice data segments Sn adjusted as described above are combined so as to overlap each other along the time base t, so that the voice playback data is generated by the voice playback data generator 441 of the voice data processing unit 311.

Figure 4H:
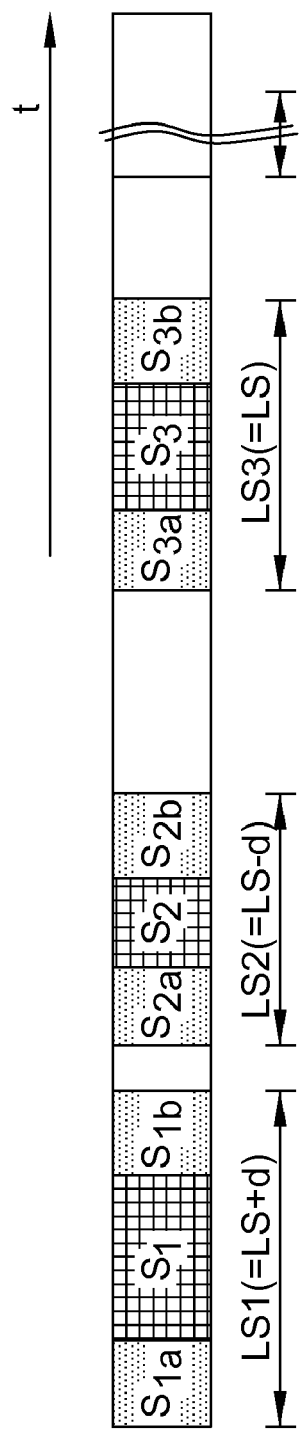

In the present embodiment, as shown in FIG. 4H, the same area as the first similarity calculation area $M_{na}$ set in the above is set as a first overlap area $S_{na}$, and the same area as the second similarity calculation area $M_{nb}$ is set as a second overlap area $S_{nb}$.

Figure 4I:
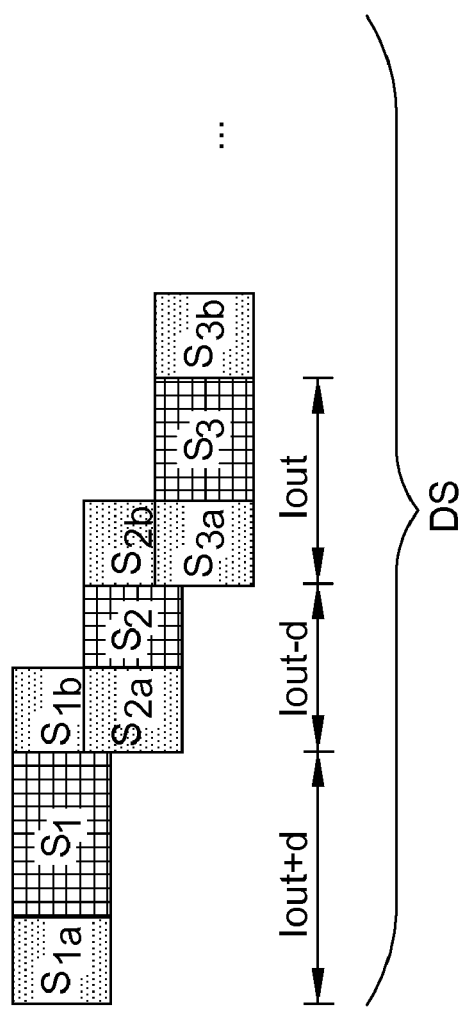
Figure 6A:
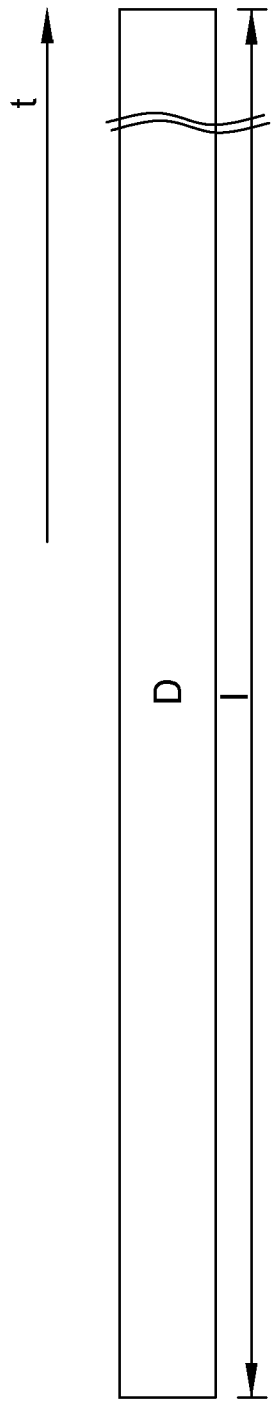
FIGS. 6A through 6E are diagrams illustrating data processing for converting voice data to voice playback data so as to correspond to a magnification of a playback velocity used to reproduce the voice data by an OLA method.
Figure 6B:
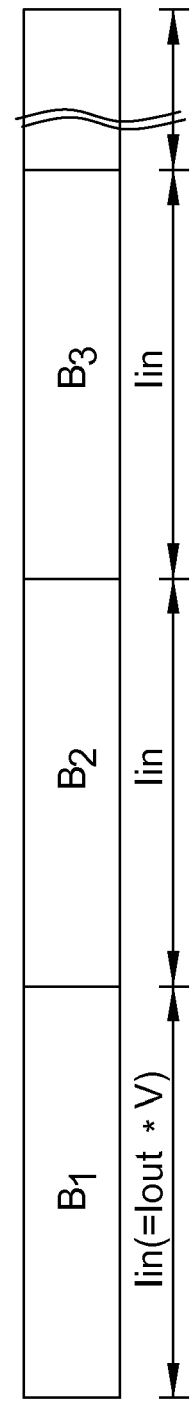
Figure 6C:
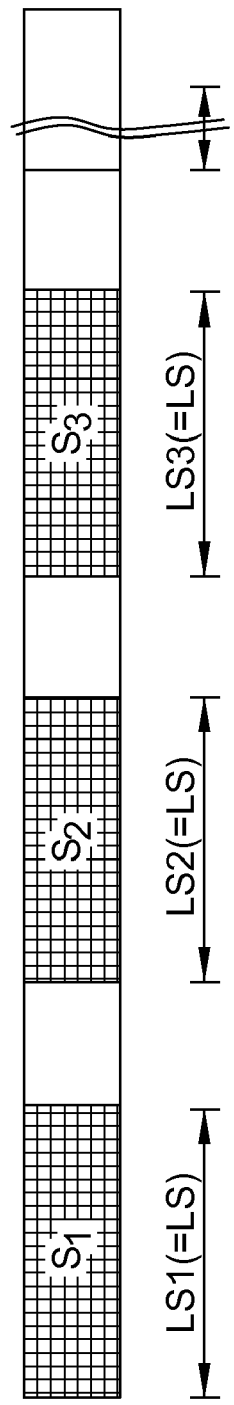
Figure 6D:
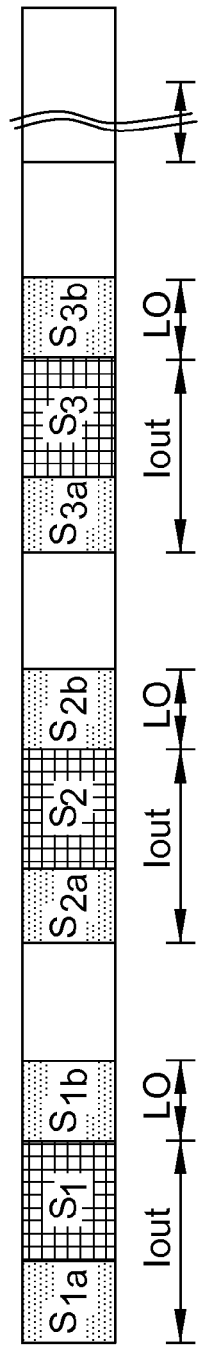
Figure 6E:
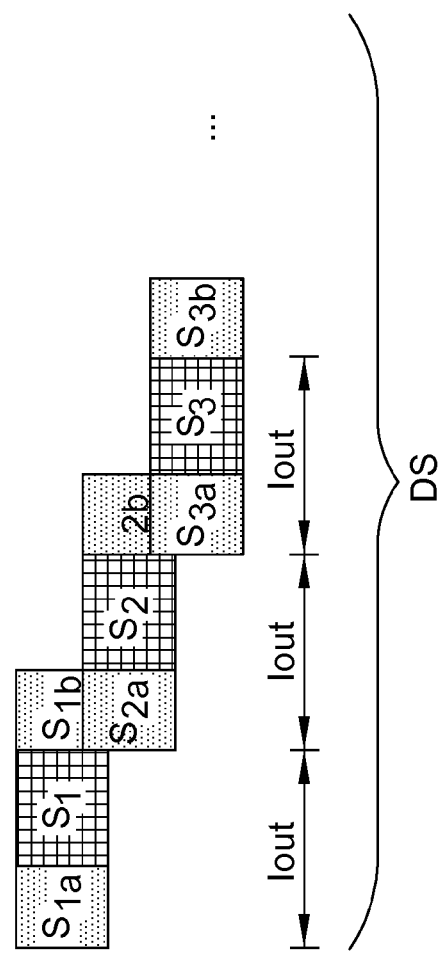
Figure 7C:
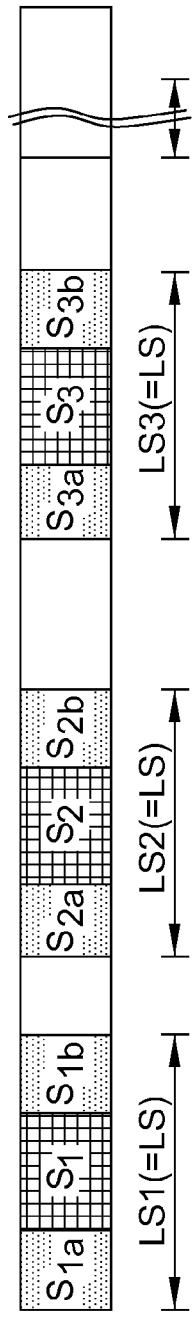
Figure 7D:
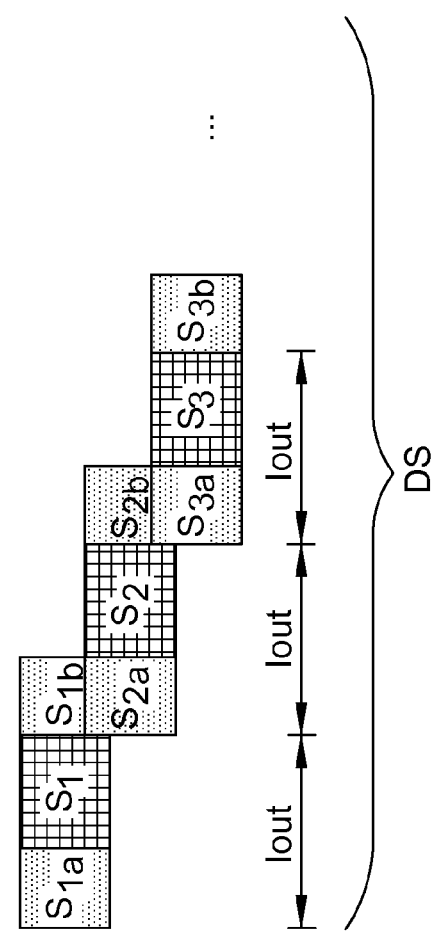
Figure 12:
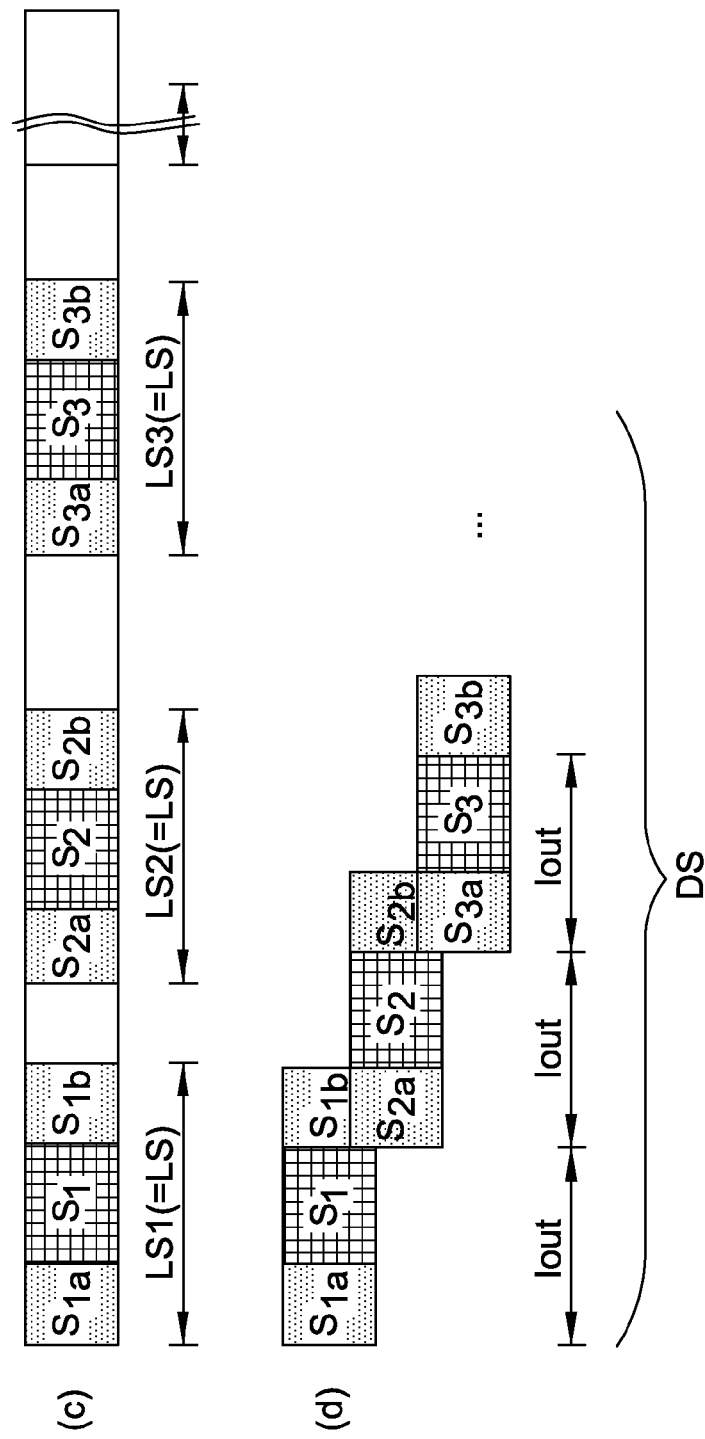
FIG. 12 is a diagram showing data processing for converting voice data to voice playback data so as to correspond to a magnification of a playback velocity used to reproduce the voice data by the WSOLA method.

Thereafter, as shown in FIG. 4I, the first overlap area $S_{na}$ and second overlap area $S_{nb}$ set as described above are sequentially combined so as to overlap each other along the time base t thereby to generate voice playback data DS.

Described concretely, a second overlap area $S_{1b}$ set to the first voice data segment $S_1$ and a first overlap area $S_{2a}$ set to the second voice data segment $S_2$ sided with the first voice data segment $S_1$ along the time base t are combined so as to overlap each other.

The respective voice data segments $S_n$ are processed sequentially in like manner. Namely, data processing is repeated in such a manner that after similar processing has been executed on the second voice data segment $S_2$ and the third voice data segment $S_3$, the third voice data segment $S_3$ and the fourth voice data segment $S_4$ are subjected to the similar processing, whereby voice playback data DS is generated.

Here, voice data in the second overlap area $S_{nb}$ provided in a stage subsequent to each of the respective voice data segments $S_n$, and voice data in a first overlap area $S_{(n+1)a}$ provided in a stage prior to its subsequent voice data segment $S_{n+1}$ are combined in a manner similar to the OLA method to normalize power of voice data in mutual overlap areas $S_{na}$ and $S_{(n+1)b}$. For example, a trapezoidal window function is added up to the respective voice data segments $S_n$, followed by execution of their combination.

Next, the playback or reproduction and output of voice are performed as shown in FIG. 3 (S71).

Here, the voice information provision unit 16 provides voice information to the subject SU, based on the voice playback data converted and outputted by the voice data processing unit 311 as mentioned above.

An imaging area of the subject SU is scanned. Here, the scan section 2 scans the subject SU thereby to acquire magnetic resonance signals. Thereafter, the image generator 312 generates a magnetic resonance image about the imaging area of the subject SU with the magnetic resonance signals acquired by the scan's execution as raw data. The display unit 33 displays the generated magnetic resonance image on its display screen.

In the present embodiment as described above, the positions and lengths on the time base, of the voice data segments $S_n$ are varied and the similarities are calculated at the varied positions. The lengths and positions of the respective voice data segments $S_n$ are adjusted in such a manner that the similarities Sm (d1, d2) calculated in the range in which the lengths and positions on the time base, of the voice data segments $S_n$ are respectively brought to the maximum value in the range in which the lengths and positions on the time base, of the voice data segments Sn have been varied. Thereafter, the respective voice data segments $S_n$ adjusted as described above are combined so as to overlap each other along the time base t thereby to generate the voice playback data DS. Thus, unlike the WSOLA method, the lengths on the time base, of the voice data segments $S_n$ are varied as well as the positions on the time base, of the voice data segments $S_n$, and the similarities are calculated at the varied positions respectively.

Thus, in the present embodiment, the voice playback data can be made continuous and the voice is reproduced in the natural pitch. It is therefore possible to improve sound quality.

Incidentally, in the above present embodiment, the magnetic resonance imaging apparatus 1 corresponds to the imaging apparatus of the invention. In the above embodiment, the scan section 2 corresponds to the scan section or unit of the invention. In the above embodiment, the voice information provision unit 16 corresponds to the voice information provision unit or provider of the invention. In the above embodiment, the voice data processing unit 311 corresponds to the voice data processing unit or processor and the voice data processing device of the invention. In the above embodiment, the voice data block setting device 411 corresponds to the voice data block setting device or setter of the invention. In the above embodiment, the segment setting device 421 corresponds to the segment setting device or setter of the invention. In the above embodiment, the segment adjuster 431 corresponds to the segment adjuster or adjusting portion of the invention. In the above embodiment, the similarity calculation area setting device 432 corresponds to the similarity calculation area setting device or setter of the invention. In the above embodiment, the similarity calculation device 433 corresponds to the similarity calculation device or calculator of the invention. In the above embodiment, the voice playback data generator 441 corresponds to the voice playback data generator or generating portion of the invention. In the above embodiment, the overlap area setting device 442 corresponds to the overlap area setting device or setter of the invention.

Upon implementation of the invention, the invention is not limited to the above embodiment. Various modifications can be adopted.

Although the above embodiment has described where the cross-correlation function values are calculated as the similarities, for example, the invention is not limited to it.

For example, an AMDF (Average Magnitude Difference Function) may be calculated as the similarity.

Although the above embodiment has described where the first similarity calculation area is set as the first overlap area and the second similarity calculation area is set as the second overlap area, the invention is not limited to them.

Although the above embodiment has shown, as an example, where the similarity calculation area setting device 432 sets the predetermined area located on the start point side on the time base, of the voice data segment, and sets the predetermined area located on the end point side on the time base, of the voice data segment as the second similarity calculation area, the invention is not limited to it. Here, the first similarity calculation area and the second similarity calculation area may be set to areas other than each voice data segment.

Although the present embodiment has described where the invention is applied to the magnetic resonance imaging apparatus, the invention is not limited to it. The invention may be applied to other imaging apparatuses such as an X-ray CT apparatus. Further, the voice data processing unit 311 according to the present embodiment may be used independently as a voice data processing device.

Many widely different embodiments of the invention may be configured without departing from the spirit and the scope of the present invention. It should be understood that the present invention is not limited to the specific embodiments described in the specification, except as defined in the appended claims.

What is claimed is:

1. A voice data processing apparatus configured to convert voice data to voice playback data using an overlap-add method to correspond to a set magnification of playback velocity, said voice data processing apparatus comprising:
    a voice data block setting device configured to partition the voice data to set a plurality of voice data blocks;
    a segment setting device configured to set voice data segments to the voice data that correspond to respective voice data blocks set by the voice data block setting device;
    a segment adjuster configured to adjust positions and lengths on a time base of the voice data segments set by the segment setting device; and
    a voice playback data generator configured to combine the respective voice data segments adjusted by the segment adjuster to overlap each other along the time base, thereby generating the voice playback data,
    wherein the segment adjuster comprises:
    a similarity calculation area setting device configured to set a predetermined area located on a side of a start point on the time base of each voice data segment set by the segment setting device as a first similarity calculation area and to set a predetermined area located on a side of an end point side on the time base of the voice data segment as a second similarity calculation area; and
    a similarity calculation device configured to calculate similarities between a waveform of voice data in the second similarity calculation area set to a first voice data segment and a waveform of voice data in the first similarity calculation area set to a second voice data segment with respect to the first and second voice data segments arranged sequentially along the time base of the voice data segments in which the first and second similarity calculation areas have been set by the similarity calculation area setting device, and
    wherein in a range in which the start and end points on the time base of the voice data segments are respectively moved along the time base, the positions and lengths on the time base of the voice data segments are adjusted based on the similarities calculated by the similarity calculation device.

2. The voice data processing apparatus according to claim 1, wherein the segment adjuster is configured to adjust the positions and lengths on the time base of the voice data segments such that each of the similarities calculated by the similarity calculation device becomes a maximum value in the range in which the start and end points on the time base of the voice data segments are respectively moved along the time base.

3. The voice data processing apparatus according to claim 1, wherein the similarity calculation device is configured to calculate cross-correlation function values of the waveform of the voice data in the second similarity calculation area set to the first voice data segment and the waveform of the voice data in the first similarity calculation area set to the second voice data segment as the similarities.

4. The voice data processing apparatus according to claim 2, wherein the similarity calculation device is configured to calculate cross-correlation function values of the waveform of the voice data in the second similarity calculation area set to the first voice data segment and the waveform of the voice data in the first similarity calculation area set to the second voice data segment as the similarities.

5. The voice data processing apparatus according to claim 1,
wherein the voice playback data generator comprises an overlap area setting device configured to set an area in which a predetermined time has elapsed since the start point of the time base at each of the voice data segments adjusted by the segment adjuster as a first overlap area, and to set an area in which a predetermined time is retraced from the end point of the time base at each voice data segment as a second overlap area, and
wherein the voice playback data generator is configured to combine the second overlap area set to the first voice data segment and the first overlap area set to the second voice data segment to overlap each other with respect to the first and second voice data segments sequentially arranged along the time base at the voice data segments adjusted by the segment adjuster, thereby generating the voice playback data.

6. The voice data processing apparatus according to claim 2,
wherein the voice playback data generator comprises an overlap area setting device configured to set an area in which a predetermined time has elapsed since the start point of the time base at each of the voice data segments adjusted by the segment adjuster as a first overlap area, and to set an area in which a predetermined time is retraced from the end point of the time base at each voice data segment as a second overlap area, and
wherein the voice playback data generator is configured to combine the second overlap area set to the first voice data segment and the first overlap area set to the second voice data segment to overlap each other with respect to the first and second voice data segments sequentially arranged along the time base at the voice data segments adjusted by the segment adjuster, thereby generating the voice playback data.

7. The voice data processing apparatus according to claim 5, wherein the overlap area setting device is configured to set the first similarity calculation area as the first overlap area and to set the second similarity calculation area as the second overlap area.

8. A voice data processing method for converting voice data to voice playback data by an overlap-add method to correspond to a set magnification of playback velocity, said voice data processing method comprising:
partitioning the voice data to set a plurality of voice data blocks;
setting voice data segments to the voice data to correspond to respective voice data blocks;
adjusting positions and lengths on a time base of the voice data segments; and
combining the respective voice data segments to overlap each other along the time base, thereby generating the voice playback data,
wherein adjusting positions and lengths of the voice data segments comprises:
setting a predetermined area located on a side of a start point on the time base of each voice data segment as a first similarity calculation area and setting a predetermined area located on a side of an end point side on the time base of the voice data segment as a second similarity calculation area, and
calculating similarities between a waveform of voice data in the second similarity calculation area set to a first voice data segment and a waveform of voice data in the first similarity calculation area set to a second voice data segment with respect to the first and second voice data segments arranged sequentially along the time base of the voice data segments in which the first and second similarity calculation areas have been set, and
wherein in a range in which the start and end points on the time base of the voice data segments are respectively moved along the time base, the positions and lengths on the time base of the voice data segments are adjusted based on the calculated similarities.

9. The voice data processing method according to claim 8, wherein adjusting positions and lengths of the voice data segments further comprises adjusting the positions and lengths on the time base of the voice data segments such that each of the calculated similarities becomes a maximum value in the range in which the start and end points on the time base of the voice data segments are respectively moved along the time base.

10. The voice data processing method according to claim 8, wherein calculating similarities comprises calculating cross-correlation function values of the waveform of the voice data in the second similarity calculation area set to the first voice data segment and the waveform of the voice data in the first similarity calculation area set to the second voice data segment.

11. The voice data processing method according to claim 8, wherein combining the respective voice data segments comprises:
setting an area in which a predetermined time has elapsed since the start point of the time base at each of the voice data segments as a first overlap area;
setting an area in which a predetermined time is retraced from the end point of the time base at each voice data segment as a second overlap area; and
combining the second overlap area and the first overlap area to overlap each other with respect to the first and second voice data segments sequentially arranged along the time base at the voice data segments, thereby generating the voice playback data.

12. The voice data processing method according to claim 11, wherein combining the respective voice data segments further comprises setting the first similarity calculation area as the first overlap area and setting the second similarity calculation area as the second overlap area.

13. An imaging apparatus configured to execute scans on an imaging area of a subject to image the imaging area of the subject, said imaging apparatus comprising:
a voice data processing unit configured to convert voice data to voice playback data using an overlap-add method to correspond to a set magnification of playback velocity; and
a voice information provision unit configured to output the voice playback data converted by the voice data processing unit to provide voice information to the subject,
wherein the voice data processing unit comprises:
a voice data block setting device configured to partition the voice data to set a plurality of voice data blocks;

a segment setting device configured to set voice data segments to the voice data that correspond to respective voice data blocks set by the voice data block setting device;

a segment adjuster configured to adjust positions and lengths on a time base of the voice data segments set by the segment setting device; and a voice playback data generator configured to combine the respective voice data segments adjusted by the segment adjuster to overlap each other along the time base, thereby generating the voice playback data, wherein the segment adjuster comprises:

a similarity calculation area setting device configured to set a predetermined area located on a side of a start point on the time base of each voice data segment set by the segment setting device as a first similarity calculation area and to set a predetermined area located on a side of an end point side on the time base of the voice data segment as a second similarity calculation area; and a similarity calculation device configured to calculate similarities between a waveform of voice data in the second similarity calculation area set to a first voice data segment and a waveform of voice data in the first similarity calculation area set to a second voice data segment with respect to the first and second voice data segments arranged sequentially along the time base of the voice data segments in which the first and second similarity calculation areas have been set by the similarity calculation area setting device, and wherein in a range in which the start and end points on the time base of the voice data segments are respectively moved along the time base, the positions and lengths on the time base of the voice data segments are adjusted based on the similarities calculated by the similarity calculation device.

14. The imaging apparatus according to claim 13, wherein the segment adjuster is configured to adjust the positions and lengths on the time base of the voice data segments such that each of the similarities calculated by the similarity calculation device becomes a maximum value in the range in which the start and end points on the time base of the voice data segments are respectively moved along the time base.

15. The imaging apparatus according to claim 13, wherein the similarity calculation device is configured to calculate cross-correlation function values of the waveform of the voice data in the second similarity calculation area set to the first voice data segment and the waveform of the voice data in the first similarity calculation area set to the second voice data segment as the similarities.

16. The imaging apparatus according to claim 13, wherein the voice playback data generator comprises an overlap area setting device configured to set an area in which a predetermined time has elapsed since the start point of the time base at each of the voice data segments adjusted by the segment adjuster as a first overlap area, and to set an area in which a predetermined time is retraced from the end point of the time base at each voice data segment as a second overlap area, and wherein the voice playback data generator is configured to combine the second overlap area set to the first voice data segment and the first overlap area set to the second voice data segment to overlap each other with respect to the first and second voice data segments sequentially arranged along the time base at the voice data segments adjusted by the segment adjuster, thereby generating the voice playback data.

17. The imaging apparatus according to claim 16, wherein the overlap area setting device is configured to set a first similarity calculation area as the first overlap area and to set a second similarity calculation area as the second overlap area.

18. The imaging apparatus according to claim 13, wherein the voice information provision unit is configured to provide voice information to the subject upon execution of each scan on the subject.

19. The imaging apparatus according to claim 13, wherein the voice data processing unit is configured to convert the voice data such that the reproduction of the voice playback data is completed during a period from a time prior to the start of the scan for the subject to a time when the scan is started.

20. The imaging apparatus according to claim 13, further comprising a scan section configured to execute the scans to acquire magnetic resonance signals from the imaging area of the subject in a static magnetic field space.

* * * * *